United States Patent [19]
Sinn et al.

[11] 3,991,173
[45] Nov. 9, 1976

[54] RADIOACTIVELY TAGGED ERYTHROCYTES AND AGENTS CONTAINING THEM

[75] Inventors: Hannsjörg Sinn, Wiesloch-Bai.; Walter Maier-Borst, Dossenheim, both of Germany

[73] Assignee: Byk-Mallinckrodt Chemische Produkte GmbH, Dietzenbach-Steinberg, Germany

[22] Filed: May 29, 1975

[21] Appl. No.: 582,028

[30] Foreign Application Priority Data
June 7, 1974  Germany............................ 2427659

[52] U.S. Cl. ..................................................... 424/1
[51] Int. Cl.² ........................................... A61K 43/00
[58] Field of Search ................. 424/1; 252/301.1 R

[56] References Cited
OTHER PUBLICATIONS

Adatepe, et al., International Journal of Radiation and Isotopes, vol. 22, pp. 498 to 501 (1971).

Barth, et al., Journal of Immunology, vol. 112, No. 2, Feb. 1974 pp. 757–762.

Eckelman, et al., American Journal of Roentgenelogy, Radium Therapy and Nuclear Medicine, vol. 118, No. 4, Aug. 1973, pp. 861–863.

*Primary Examiner*—Leland A. Sebastian
*Assistant Examiner*— Lloyd
*Attorney, Agent, or Firm*—R. J. Klostermann; L. N. Goodwin

[57] ABSTRACT

Radioactively tagged erythrocytes suitable for scintigraphic display.

13 Claims, No Drawings

RADIOACTIVELY TAGGED ERYTHROCYTES AND AGENTS CONTAINING THEM

BACKGROUND OF INVENTION

1. Field of Invention

This invention relates to radioactively tagged erythrocytes and to a process for their preparation. The invention also relates to agents which contain these tagged erythrocytes and which are suitable for scintigraphic display, and to a process for producing these agents.

2. Description of Prior Art

The determination of erythrocyte volume, of erythrocyte survival time, and the detection of an enteral blood loss as well as scintigraphically displaying the blood pool and spleen are routine methods in nuclear medicine which are carried out with radioactively tagged erythrocytes. Methods of this kind are described, for example "Haematologie" by H. Heimpel and in Nuklearmedizinische Funktionsdiagnostik by D. Emrich, George Thieme Verlag, Stuttgart 1971. In methods of this kind, there has to be, on the one hand, a stable bond between the radioactive isotope and the erythrocytes. On the other hand the isotope used has to have suitable physical properties, above all in regard both to the energy of the gamma rays emitted and to half life. It is already known that $51_{Cr}$ can be used for tagging erythrocytes. Corresponding methods are described, for example, by Gray, S and K Sterlin in "The tagging of red cells and plasma proteins with radioactive chromium" by J. clin. Invest. 29, 1604 (1950). In the $51_{Cr}$ used for this purpose, the bond between isotope and erythrocytes is very strong. Unfortunately, this isotope gives off a high level of radiation during investigation on account of its long half life of 27.8 days. Attempts have already been made to tag erythrocytes with the $99m_{Tc}$ readily available through generators, cf. for example Bull, U., K. W. Frey, H. Langhammer, K. J. Pfeiffer and N. Napp: "Zur Problematik und Methodk der Milzszintigraphie und $99m_{Tc}$-markierten, warmealterierten Erythrocyten" Fortschr. Rontgenstr. 117, 1 (1972) 86. In this radionuclide, however, the strength of the bond with the erythrocytes is very weak and cannot be compared with that of $51_{Cr}$. Accordingly, tagging with $99m_{Tc}$ has only been carried out on a limited scale in the past.

Accordingly, the object of the invention is to obviate the disadvantages referred to above and, in particular, to provide an agent for functional diagnosis in nuclear medicine in which there is a bond of high strength between the radionuclide and the erythrocyte. This object is substantially achieved by the invention.

BRIEF DESCRIPTION OF INVENTION

Accordingly, the invention relates to radioactively tagged erythrocytes which are tagged with radio isotopes of gallium, indium or thallium. In one preferred embodiment of the invention, the erythrocytes are tagged with gallium or indium. In another preferred embodiment of the invention, the erythrocytes are tagged with gallium or thallium. Finally, in yet another preferred embodiment of the invention, the erythrocytes are tagged with indium or thallium.

According to the invention, these radioactively tagged erythrocytes can be obtained by adding an isotonic common salt solution or a plasma expander and a complex former to erythrocyte sediments obtained in the usual way, introducing a solution of a trivalent radioactive isotope into the solution thus obtained, incubating the resulting mixture and separating off the tagged erythrocytes.

The invention also provides a scintigraphic agent which, in addition to physiological common salt solution or a solution of a plasma expander, contains the radioactively tagged erythrocytes described above. This agent can be obtained by suspending the tagged erythrocytes obtained in the manner described above in physiological common salt solution or in a solution of a plasma expander, for example polyvinyl pyrrolidone.

Finally, the invention provides a test kit which contains the acetyl acetone solution required for tagging in buffer solution accommodated in sterile and pyrogen-free form in ampoules. The erythrocyte sediment obtained in the usual way is added to this test kit, followed by addition of the corresponding quantity of the solution of the radioactive isotope.

DETAILED DESCRIPTION OF INVENTION

Accordingly, the invention relates to the use of radioactive isotopes of trivalent elements of the Main Group of the Periodic System, more especially gallium, indium and thallium, above all indium and gallium, for the stable tagging of erythrocytes. In the case of indium and gallium, in contrast to technetium, the oxidation stages do not undergo any change in aqueous medium, so that stable solutions are guaranteed.

In addition, it is possible to select the suitable isotope according to the particular problem. Thus, tagging agents with the required half life can be obtained, for example, by using the isotopes $113m_{In}$, $111_{In}$ and $114m_{In}$ with half lives of 1.7 h, 1.8 and 50 days, respectively.

The simple tagging process on which the invention is based is designed to be carried out with kits in order to maintain sterility and freedom from pyrogens. Both the in-vitro and the in-vivo tests of the erythrocytes tagged with indium and gallium isotopes according to the invention are indicative of a bond strength equivalent with or superior to that obtained in tagging with $51_{Cr}$. The generally suitable tagging with $113m_{In}$ in the form of a generator eluate of the type available in numerous nuclear medicine laboratories, guarantees an extremely favourable, low radiation level during examination of the patient.

According to the invention, tagging with erythrocytes is carried out by adding an isotonic common salt solution or a solution of a plasma expander, for example polyvinyl pyrrolidone, and a solution of a suitable complex former in a suitable buffer to an erythrocyte sediment obtained in the usual way. The erythrocyte sediments may be prepared, for example, as described by H. Heimpel in "Haematologie" and by D. Emrich in "Nuklear-medizinische Funktionsdiagnostik", Georg Thieme Verlag, Stuttgart 1971. Preferred complex formers are diketones of the general formula R—CO—CH$_2$—CO—R' where R and R' are short-chain aliphatic radicals or phenyl groups.

It is preferred that the aliphatic radicals contain 1 to 6 carbon atoms. Alkyl groups containing 1 to 4 carbon atoms are especially preferred, such as methyl, ethyl, propyl and butyl.

Further information on complexes and complex formers of this kind may also be found in "Stability Constrants" Special Publications 17 (1964) London, Chemical Society, Burlington House, NW1 which is incorporated herein by reference. One preferred complex former is, for example, acetyl acetone, i.e. 2,4-pentane dione. The complex former used is present for example in a concentration of from 0.01 to 0.1 m in a buffer solution with a pH value of 7 to 8.

A suitable quantity of a solution of a trivalent radioactive isotope (for example $113m_{In}$ from a generator) to provide an activity of about 1 mCi to about 100 mCi/cc of erythrocytes sediment is added to the mixture thus obtained. Generators of this kind are manufactured and marketed, for example, by Byk-Mallinckrodt. The radionuclide $113m_{In}$ may be taken from an $113_{Sn}$-$113m_{In}$ generator in which the radionuclide $113m_{In}$ is continuously formed by the conversion of Sn113. Separation is carried out by eluting the isotopes absorbed in a column filled with silica gel. Solutions of the radio isotopes in the form in which they are taken from these generators normally contain from $10^{-10}$ to $10^{-14}$ g/ml of radio isotope in sterile pyrogen-free 0.05 N HCl. After mixing and brief incubation at 15° to 30° C, preferably at room temperature, the erythrocytes may be separated by centrifuging and washed once with common salt solution. After making up to the original volume with isotonic common salt solution or a solution of a plasma expander, for example polyvinyl pyrrolidone, the erythrocyte suspension is ready for reinjection. All the stages involved in tagging are carried out under sterile conditions.

The new process is distinguished by its simplicity. A high level of stability is obtained in the tagged erythrocytes and is not affected by repeated washing, prolonged storage or by denaturation under heat as required for scintigraphy of the spleen. This prompts the conclusion that, where tagging is carried out with trivalent elements, especially with indium isotopes, the nuclide is not fixed to the cell membrane, but instead the isotope used is in such a complex, bound form that the erythrocyte membrane can be traversed and the radio isotope is bound by the proteins inside the cell. It has been possible to confirm this assumption by haemolysis of the tagged erythrocytes, followed by centrifuging for 30 minutes at 40,000 G. The resulting supernatant phase has 88.5% of the original activity in the case of 111 In-tagged erythrocytes, in other words only a very small proportion of the activity is present in the sediment, i.e. the membranes. The same may be assumed for erythrocytes tagged with radionuclides of gallium, for example $67_{Ga}$ or of thallium.

According to the invention, it is essential to use a complex former because the complex former enables the radio isotope to penetrate through the cell membrane. Parallel tests conducted without complex formers produce a tagging yield of approximately 30% and considerably higher wash-out rates. Tables 1 to 3 below contain particulars on the tagging yield, the wash-out rate and the stability of the tagged erythrocytes where $111_{In}$ is used.

Table 1

| $^{111}$In-Ery- | | | | | | | | |
|---|---|---|---|---|---|---|---|---|
| Sed. (%) | 97.4 | 94.5 | 97.3 | 95.0 | 98.8 | 99.4 | 99.4 | MW 97.4 |
| Supernatant Phase (%) | 2.5 | 5.2 | 2.7 | 4.9 | 1.2 | 0.4 | 0.5 | MW 2.5 |

$^{111}$In tagging rates of the erythrocytes of 7 test specimens, expressed in percent of the original activity.

Table 2

| n = 5 | Tagging rate | Washes | | | |
|---|---|---|---|---|---|
| | | 1 | 2 | 3 | 4 |
| Erys (%) | 97.4 | 99.5 | 99.4 | 99.4 | 99.5 |
| Supernat. (4) | 2.5 | 0.5 | 0.5 | 0.5 | 0.5 |

Percentage $^{111}$In-bonding to erythrocytes after 4 washes each with 7 ml of an isotonic NaCl solution.

Table 3

| | Room Temp. | + 4° C. |
|---|---|---|
| Ery (%) | 98.6 | 99.5 |
| Supernat. | 1.5 | 0.3 |

In-vitro stability of the $^{111}$In-tagged erythrocytes after storage for 24 hours at room temperature and + 4° C.

The Tables show that it is possible in accordance with the invention to obtain an extremely high tagging yield coupled with a negligibly low wash-out rate. The in-vitro stability of the tagged erythrocytes over a period of 24 hours at room temperature and at +4° C. shows extremely good values. This is also the case where other radionuclides of gallium, indium and/or thallium, for example $67_{Ga}$, are used. In their case, too, improvements are obtained both in the tagging yield and in the stability of the tagged erythrocytes.

On the basis of the quantitative ratios quoted above, it may be assumed that on a statistical average each of the erythrocytes is tagged because 1 cc of sediment is known to contain $4.5 - 5 \times 10^9$ erythrocytes.

The invention is illustrated in the following Examples

EXAMPLE 1

Reaction solution 0.3 ml of acetyl acetone are added to 25 ml of a 1 m tris-(hydroxymethyl)-amino methane buffer solution. This solution is adjusted with 1 N HCl to a final pH-value of 7.6, made up to 100 ml with twice-distilled water and sterilised by membrane filters (pore size $0.2\mu$). This solution may be stored for several weeks in fused glass ampoules.

Erythrocyte tagging 4 ml of blood are taken from a vein with a 5 ml syringe. After careful mixing, the blood is transferred to a 10 ml centrifuge tube and diluted with 4 ml of isotonic common salt solution. After centrifuging for 6 minutes at 1000 G, the supernatant phase is removed, the erythrocytes resuspended in 6 to 7 ml of isotonic common salt solution and centrifuged off again. 5 ml of isotonic common salt solution, 1 ml of the reaction solution and 1 ml of 0.05 N HCl-acid eluate with an activity of 1–100 mCi from a 113 m In generator of the kind described above, are added to the erythrocyte sediment thus obtained. After careful mixing and incubation for 20 minutes at room temperature, the erythrocytes are centrifuged off and washed once with isotonic common salt solution. Reinjection is carried out after the erythrocyte sediment has been made up to its original volume of 4 ml with isotonic common salt solution or with the supernatant phase from the first centrifuging step. All stages involved in tagging have to be carried out under sterile conditions.

EXAMPLE 2

The reaction solution is prepared in accordance with Example 1.

For erythrocyte tagging, 1 ml of a 0.05 N HCl-acid carrier-free solution of $111_{InCl_3}$ with an activity of 1–100 mCi is added to the mixture of erythrocyte suspension and reaction solution, followed by careful mixing and incubation for 20 minutes at room temperature. The solution is then further treated in the same way as described above.

EXAMPLE 3

The reaction solution is prepared in the same way as described in Example 1. For erythrocyte tagging, 1 ml of a 0.05 N carrier-free solution of $67_{GaCl_3}$ with an activity of 1–100 mCi is added to the mixture of erythrocyte suspension and reaction solution, followed by careful mixing and incubation for 20 minutes at room temperature. The erythrocytes are further treated in the same way as described in Example 1.

As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. Radioactively tagged erythrocytes, tagged with radioactive isotopes of gallium, or thallium.

2. Radioactively tagged erythrocytes as claimed in claim 1, in which the tagging isotope is $67_{Ga}$.

3. A process for the preparation of radioactively tagged erythrocytes tagged with a radioactive isotope of gallium, indium or thallium wherein an isotonic sodium chloride solution or a plasma expander and a complex former are added to erythrocyte sediments, a solution of a radioactive isotope of gallium, indium or thallium is introduced into the resulting solution, the mixture thus obtained is incubated and the tagged erythrocytes separated off.

4. A process as claimed in claim 3 in which a solution of $111_{In}$, $113m_{In}$ or $114m_{In}$ is used.

5. A process as claimed in claim 3, in which a solution of $67$ Ga is used.

6. A process as claimed in claim 3 in which the complex former used is a diketone of the general formula $R-CO-CH_2-CO-R'$ where R and R' are short-chain aliphatic radicals or phenyl groups.

7. A process as claimed in claim 3 in which a carrier-free solution of the radionuclide with an activity of 1–100 mCi is used for tagging.

8. An agent for scintigraphic display, containing in addition to an isotonic sodium chloride solution or a plasma expander, a radioactively tagged erythrocyte of the kind claimed in claim 1.

9. A process for the preparation of an agent for scintigraphic display, in which isotonic sodium chloride solution or a plasma expander and a complex former are added to erythrocyte sediments, a solution of a radioactive isotope of gallium, indium or thalium is introduced into the resulting solution, the mixture thus obtained is incubated, the tagged erythrocytes are separated off and the tagged erythrocytes obtained are resuspended in isotonic sodium chloride solution or a plasma expander.

10. A process as claimed in claim 9, in which a solution of $111_{In}$, $113m_{In}$ or $114m_{In}$ is used.

11. A process as claimed in claim 9, in which a solution of $67_{Ga}$ is used.

12. A process as claim in claim 9, in which a solution of the radionuclide with an acitivity of 1 to 100 mCi is used.

13. An agent for scintigraphic display containing in addition to an isotonic sodium chloride solution or a plasma expander and a complex former a radioactively tagged erythrocyte tagged with a radioactive isotope of gallium, indium or thalium.

* * * * *